(12) United States Patent
Stewart

(10) Patent No.: US 7,476,782 B2
(45) Date of Patent: Jan. 13, 2009

(54) FODDER RADISH

(75) Inventor: Alan Vincent Stewart, Christchurch (NZ)

(73) Assignee: Pyne Gould Guinness Limited, Christchurch (NZ)

( * ) Notice: Subject to any disclaimer, the term of this patent is extended or adjusted under 35 U.S.C. 154(b) by 149 days.

(21) Appl. No.: 10/851,719

(22) Filed: May 20, 2004

(65) Prior Publication Data

US 2005/0022268 A1  Jan. 27, 2005

(30) Foreign Application Priority Data

Jul. 24, 2003 (AU) ............... 2003903841

(51) Int. Cl.
*A01H 5/00* (2006.01)
*A01H 5/10* (2006.01)
*A01H 1/00* (2006.01)

(52) U.S. Cl. .............. 800/306; 800/260; 800/298

(58) Field of Classification Search ........ 800/298, 800/306, 260, 295
See application file for complete search history.

(56) References Cited

U.S. PATENT DOCUMENTS

| | | | |
|---|---|---|---|
| 5,304,719 A * | 4/1994 | Segebart | 800/303 |
| 5,367,109 A * | 11/1994 | Segebart | 800/320.1 |
| 5,763,755 A * | 6/1998 | Carlone | 800/320.1 |
| 5,850,009 A * | 12/1998 | Kevern | 800/271 |

OTHER PUBLICATIONS

Johnston. Welsh Plant Breeding Station Annual Report, pp. 135-139, 1963.*
McNaughton. 1974. Cruciferae Newletter 1: 21-22.*
A. Bonnet, Inheritance Of Some Characters In Radish, Newsletter, 1979, 4:31.
R. A. T. George, et al., A Classification Of Winter Radish Cultivars, Euphytica 30, 1981, p. 483-492.
T. D. Johnson, Breeding Aspects Of *Raphanus* And *Brassica*, Cruciferae Newsletter 2, p. 13.
T. D. Johnson, The Fodder Radish, Welsh Plant Breeding Station Annual Report, 1963, p. 135-139.
I. H. McNaughton, The Possibility Of Leafy, Biennial Radishes From Hybridisation Of *Raphanus sativus* (fodder radish) and *R. mantimus* (sea radish) Cruciferae Newsletter 1, p. 21-22.
N. F. G. Rethman, et al., Grazing Of *Raphanus sativus*. L (Japanese Radish) Journal of the Grassland Society Of South Africa, 4, p. 154.
A. Verschoor, et al., Forage Potential Of Japanese Radish (*Raphanus sativus*) As Influenced By Planting Date And Cultivar Choice, Journal Of The Grassland Society Of South Africa 9, p. 176-177.

* cited by examiner

*Primary Examiner*—David H Kruse
*Assistant Examiner*—Keith O. Robinson
(74) *Attorney, Agent, or Firm*—Frommer Lawrence & Haug LLP; Thomas J. Kowalski

(57) ABSTRACT

The invention relates to a fodder radish. More particularly, a fodder radish (*Raphanus* species) suitable for use as a multiple grazing fodder crop for livestock is provided. The invention also relates to the seeds, and to the plants of the radish. It also relates to methods of producing a *Raphanus* plant type having the characteristics of recovery from grazing to give the potential for multiple grazings over many cycles.

3 Claims, 4 Drawing Sheets

FODDER RADISH

CROSS-REFERENCE TO RELATED APPLICATIONS

This application claims priority from Australian Patent Application No. AU 2003903841, filed on May 24, 2003.

All of the foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The invention relates to a fodder radish. More particularly, a fodder radish (*Raphanus* species) suitable for use as a multiple grazing fodder crop for livestock is provided. The invention also relates to the seeds, and to the plants of the radish. It also relates to methods of producing a *Raphanus* plant type having the characteristics of recovery from grazing to give the potential for multiple grazings over many cycles.

BACKGROUND OF THE INVENTION

Animal producers worldwide use fodder crops as an inexpensive means of feeding animals during times of forage shortfall, usually during dry summer periods or during cold winter periods. Fodder crops which can be grazed many times rather than once only have potential to lower the cost of production for many farmers.

Plants of *Raphanus* are used widely throughout the world for many purposes.

For example, *Raphanus sativus*, domestic radish is used as a vegetable for human consumption, predominantly the root but also to a lessor extent of the leaves, stems and pods.

*Raphanus sativus* can also be used as an oilseed crop where the seed is harvested and oil extracted. The sprouted seed may also be consumed as a sprout by humans.

*Raphanus sativus* is also used as a biofumigant in crop rotations to suppress pathogens such as fungal diseases, or cyst nematodes in subsequent crops particularly with Sugar Beet (*Beta vulgaris*) in Europe. These crops are frequently ploughed under but may also be grazed once.

*Raphanus sativus* may be used as a single grazing fodder crop. However, the cultivars used will usually not recover sufficiently from grazing to allow multiple grazings. Many of these cultivars are relatively early to flower, bolting with 3 months of sowing. The cultivars usually also have hairy leaves and stems which on occasion can be prickly and rejected by grazing animals.

*Raphanus sativus* with large bulbs may be grown for animal fodder, notably in South Africa. The cultivars used are relatively early flowering and will usually bolt to flower within 3 months of sowing.

The nutritive value of fodder radish for animal feed is known to be high and the species possesses some valuable characteristics for livestock farming. However it is clear that there are a number of features of existing cultivars which have limited its ability to provide a flexible source of grazing on farms.

The typical radish used for grazing purposes is an annual which bolts to flower very readily and rapidly. This limits its use to a single grazing before flowering as the nutritional value declines considerably at flowering. Later flowering forms would provide more flexibility on farm by allowing farmers to keep the feed until needed. This is very apparent in the related *Brassica* species fodder rape (*Brassica napus*), turnip (*Brassica rapa*) and kale (*Brassica oleracea*) where both annual and biennial forms exist. As a result in these species the biennial forms are more widely used for animal fodder than the annual forms. The delayed flowering of the biennials allows the energy they assimilate to accumulate into storage organs such as bulbs, leaf or stems. From this perspective later flowering or biennial radishes with a long growing period would be valuable for grazing over the summer, or kept until autumn and winter in a nutritious vegetative state.

When typical fodder radish crops are grazed by animals the growing point of the plant is above ground and it is damaged, limiting any regrowth. It would be valuable for a plant to have multiple low growing points to avoid grazing damage and allow maximum recovery.

The majority of traditional fodder and vegetable radish forms of *Raphanus sativus* are covered in short prickly hairs or trichomes and this feature can render the plant less palatable to livestock than glabrous types. *Raphanus* plants which lack trichomes are preferred by grazing livestock.

SUMMARY OF THE INVENTION

It is an object of the invention to provide a better fodder radish plant for livestock grazing which can be grazed more than once or to at least provide the public with a useful choice.

The invention provides a fodder *Raphanus* plant which can be grazed more than once by livestock.

The invention also provides seeds, pollen, ovules and vegetative propagules of the plant.

The fodder radish is preferably *Raphanus* species.

Within this specification the term *"Raphanus"* is intended to include any radish species including but not limited to *Raphanus sativus, Raphanus maritimus, Raphanus landra* and *Raphanus raphanistrum*.

The *Raphanus* is preferably very late flowering or biennial in habit which allows grazing over a longer period than more rapidly flowering or annual crops.

The *Raphanus* preferably has a low crown to allow recovery from grazing by livestock.

The *Raphanus* preferably has multiple growing points to enhance the ability to recover from grazing by livestock.

The *Raphanus* preferably has minimal leaf and stem trichomes (or hairs) to enhance the palatability of the plant to grazing livestock.

The invention also provides fodder radish which can be multiply grazed and which has at least one of the following characteristics:
 a) palatable and nutritious;
 b) able to establish quickly under diverse field conditions;
 c) provide a useful amount of fodder into a drought period;
 d) tolerant or resistant to common pests, viruses and diseases affecting Brassica crops;
 e) persistent over a number of grazing cycles;
 f) provide a useful amount of fodder during the winter period;
 g) have a yellow seed coat;

h) have minimal anthocyanin expression anywhere on the plant; or i) recovers to produce a useful amount of herbage.

The *Raphanus* species may contain genetic introgression from other species such as *Brassica*.

The invention provides the plant or its parts producing seed, pollen of the plant, an ovule of the plant and vegetative propagules of the fodder species adapted for multiple grazing.

In particular the invention provides a *Raphanus* seed designated PG545.

The invention also provides a *Raphanus* plant having all the physiological and morphological characteristics of the *Raphanus* plant derived from the seed of the *Raphanus* PG545.

The invention also provides a method for producing a hybrid *Raphanus* seed which seed produces a plant capable of being multiple grazed, comprising crossing a first parent *Raphanus sativus* plant with a second parent *Raphanus* plant and harvesting the resultant hybrid *Raphanus*.

The invention also provides a hybrid seed produced by the method above.

The invention also provides a hybrid plant or its parts produced by growing said hybrid *Raphanus* seed above.

The invention also provides vegetative propagules of the fodder *Raphanus* species.

The invention also provides a method for the production of *Raphanus* with the ability to regrow after grazing to be suitable for multiple grazing which comprises:
a) crossing or backcrossing *Raphanus sativus* with *Raphanus maritimus* to produce hybrid plants
b) selecting for low crown and improved recovery from grazing in the progeny over subsequent generations The invention also provides a method of the production of *Raphanus* cultivars with glabrous leaves which comprises:
a) crossing or backcrossing the common phenotype with trichomes on the leaves of *Raphanus* with *Raphanus* plants containing genes for glabrous leaves to produce hybrid plants
b) selecting for the presence of glabrous leaves in the progeny of subsequent generations The invention also provides a method of the production of *Raphanus* with an extremely late flowering behaviour which comprises:
a) crossing or backcrossing the common early flowering *Raphanus* with extremely late flowering *Raphanus* plants to produce hybrid plants
b) selecting for late flowering in the progeny of subsequent generations The invention further provides the plant or its parts producing tetraploid seed or pollen for the production of tetraploid seed of the fodder *Raphanus* which can be multiply grazed by livestock.

The invention further provides an ovule of the tetraploid plants and vegetative propagules of the tetraploid plants.

The invention also provides a tetraploid *Raphanus* plant having all the physiological and morphological characteristics of a *Raphanus* plant derived from the seed of the *Raphanus* which can be multiply grazed by livestock.

The invention also provides a method for producing a tetraploid hybrid *Raphanus* seed comprising crossing a tetraploid first parent *Raphanus* plant with a second parent tetraploid *Raphanus* plant and harvesting the resultant hybrid Raphanus seeds, wherein said first or second parent *Raphanus* plant a tetraploid *Raphanus* plant which can be multiply grazed by livestock.

The invention also provides a tetraploid hybrid seed produced by any method above.

The invention also provides a tetraploid hybrid plant or its parts produced by growing hybrid *Raphanus sativus* seed produced by any method above.

The invention also provides vegetative propagules of tetraploid plants.

Preferably the fodder *Raphanus* plant is grown from the seed PG545. It may be grown however from any seed having these characteristics such as, for example PG534 and PG560.

The invention will now be described by way of example only with reference to the following embodiments.

BRIEF DESCRIPTION OF THE FIGURES

The following Detailed Description, given by way of example, but not intended to limit the invention to specific embodiments described, may be understood in conjunction with the accompanying Figures, incorporated herein by reference, in which.

DETAILED DESCRIPTION OF THE INVENTION

Figure 1:
FIG. 1 shows plants of the multiple graze radish in the second summer after sowing, showing the survival alongside winter forage cultivars of rape (*Brassica napus*) and leaf turnip (*Brassica rapa*), both of which had failed to survive into the second summer.
Figure 2:
FIG. 2 shows a cow grazing multigraze forage radish.
Figure 3:
FIG. 3 shows a clipped plant of multiple grazing radish showing the many stems developing from a large crown.
Figure 4:
FIG. 4 shows a single crown of multigraze radish showing the multiple regrowth sites after five grazing cycles.
Figure 5:
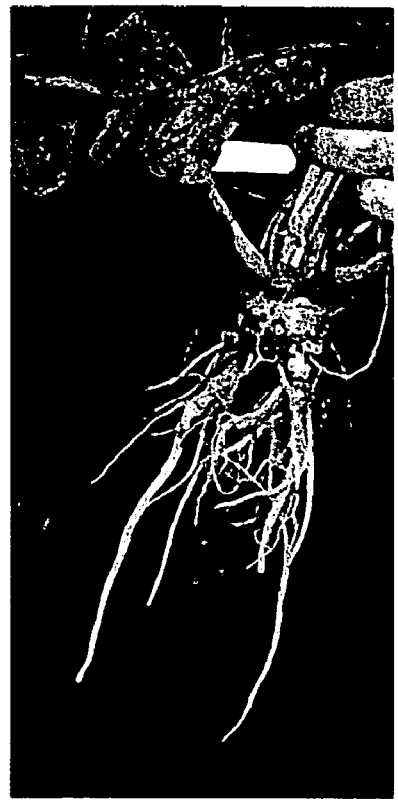
FIGS. 5 and 6 show roots of the multigraze radish showing the branched nature of the root and large crown with many emerging stems.
Figure 6:
Figure 7:
FIG. 7 shows a plant of multiple grazing radish showing the multiple stems developing from a large crown after five grazing cycles.

As used herein, the terms "comprises", "comprising", and the like can have the meaning ascribed to them in U.S. Patent Law and can mean "includes", "including" and the like.

In order to develop a multiple grazing fodder radish it was necessary to obtain a series of parental germplasm lines which contained the range of necessary features, or "phenotypes". The necessary features were available in 2 different *Raphanus* species:

| Feature | *Raphanus maritimus* | *Raphanus sativus* |
| --- | --- | --- |
| Very Late flowering | + | Mostly − few + |
| Multiple growing points | + | − |
| Deep crown | + | − |
| Forked root | + | − |
| Persistent for 2 years | + | − |
| Regrowth from grazing | + | − |
| Trichomes (unpalatable hairs) | − | Mostly − few + |
| Dehiscent pods | − | + |
| Harvestable seed | − | + |

*Raphanus maritimus* occurs on the sea coast of Europe and southern England. It has features which are of valuable for multiple grazing purposes such as a very low crown and a deep forked root. It is also very late to flower and may survive up to 2 or more years. It also has useful amounts of salt tolerance. However, it can not be used directly for grazing due to the extreme prickly nature of the trichomes (leaf hairs) on the leaves and stem and the silique or pods are non-dehiscent and do not release the seed and must be sown as pod pieces making it difficult to domesticate the plant for modem agriculture. In order to take advantage of the desirable features it is necessary to first cross this species with domesticated *Raphanus sativus* to combine the useful features into one population. These two species had previously been successfully crossed, indicating that no crossing barrier existed between the species (McNaughton 1976).

*Raphanus sativus* used for production have dehiscent pods enabling a high seed yield. They are also rapid to establish and many cultivars have a high forage yield for a single grazing. These features are of value for a multiple grazing radish.

Within *Raphanus sativus* there is a variation in the number of plant trichomes (hairs on the leaf and stem). Glabrous forms are more palatable to grazing animals and are desirable in a multiple grazing fodder radish. The glabrous form Biser was used as a source of this feature in crosses. This feature of Biser originated as a result of introgression from cabbage (*Brassica oleracea*) (Bonnet 1979). Although this source was used it would be possible to use other glabrous sources of germplasm.

Within *Raphanus sativus* there is a large variation for flowering time. Most forms are early flowering but less common late flowering forms requiring a degree of vernalisation also exist. For a multiple grazing fodder radish late flowering forms are desirable and a selection for very late flowering within Long Black Spanish were used as a basis of late flowering in subsequent crosses. Although this source was used it would be possible to use other late flowering sources of germplasm.

To obtain all the necessary features of *Raphanus sativus* which are of value for a multiple grazing fodder radish it was necessary to cross 2 populations together and select for the desirable features. The very late flowering selection from Long Black Spanish was crossed with the glabrous line Biser. This gave a late flowering glabrous radish suitable for crossing with *Raphanus maritimus*.

Further selection over 4 cycles gave a very late flowering glabrous radish. The population resulting from 3 cycles of selection was crossed with *Raphanus maritimus* and selected over 3 cycles for glabrous leaves and late flowering. However, this population still had a proportion of non-dehiscent pods so was crossed back to the $4^{th}$ cycle of selection from the late flowering selection from Black Spanish cross Biser.

This population was then selected for all the features required in a multiple grazing radish, including the following:
Late flowering habit with a long vegetative period
A deep large forked root with a low crown
Multiple growing points
Recovery from grazing over many cycles
Glabrous leaves
A dehiscent pod or silique for ease of seed harvest
High forage yield
The ability to survive for more than 1 year in suitable environments
High disease and pest resistance
Rapid establishment
Yellow seed coat
Low expression of anthocyanin pigment on all parts of the plant This resulted in 3 multiple grazing radish lines PG534, PG545 and PG560. Seed of these are deposited in the Margot Forde Germplasm Centre at AgResearch, Palmerston North, New Zealand. Seed of PG534, PG545 and PG560 were also deposited under the terms of the Budapest Treaty with the Agricultural Research Service Culture Collection (NRRL), 1815 North University St., Peoria, IL. Deposited seed will be irrevocably and without restriction or condition released to the public during the term of any patent issued from this application.

The invention has resulted from a series of complex crosses and selection from a range of germplasm sources and species over 16 years, as outlined in the breeding history of Table 1. All crosses were carried out in the field by placing a few plants of one parent among many plants of the other parent. A high selection pressure was maintained with between 1000 and 1 million plants being planted in each generation. Each cycle of selection resulted in 7 to 20 parents, which were allowed to interpollinate together in isolation.

The resulting selections have a complex origin incorporating germplasm from three species in the approximate proportions as determined by pedigree; *Raphanus sativus* (86.7%), *Raphanus maritimus* (7.5%) and *Brassica oleracea* (5.8%).

Although this Figure outlines the crosses and selections undertaken to develop the multiple grazing fodder radish it would be possible to develop such types using slightly different materials and methods. It would be important to use germplasm lines which contain all the desirable features as outlined above and then cross between them and to select for a combination of these features over many cycles of selection.

Whilst the invention has been described with reference to specific embodiments, it will be appreciated that numerous modifications and variations can be made to these embodiments without departing from the scope of the invention as described in this specification and the following claims.

The invention is further described by the following numbered paragraphs:

1. A fodder *Raphanus* plant which can be grazed more than once by livestock.
2. A fodder *Raphanus* plant according to paragraph 1 that is a *Raphanus* species selected from the group *Raphanus sativus*, *Raphanus maritimus*, *Raphanus landra* and *Raphanus raphanistrum*.
3. A fodder *Raphanus* plant according to paragraph 1 that is very late flowering or biennial in habit which allows grazing over a longer period than more rapidly flowering or annual crops.
4. A fodder *Raphanus* plant according to paragraph 1 that has a low crown to allow recovery from grazing by livestock.
5. A fodder *Raphanus* plant according to paragraph 1 that has multiple growing points to enhance the ability to recover from grazing by livestock.
6. A fodder *Raphanus* plant according to paragraph 1 that has minimal leaf and stem trichomes (or hairs) to enhance the palatability of the plant to grazing livestock.
7. A fodder radish that can be grazed many times and which recovers to produce a useful amount of herbage.
8. A fodder radish that can be multiply grazed and which has at least one of the following characteristics:
    a) palatable and nutritious;
    b) able to establish quickly under diverse field conditions;
    c) provide a useful amount of fodder into a drought period;
    d) tolerant or resistant to common pests, viruses and diseases affecting *Brassica* crops;
    e) persistent over a number of grazing cycles;
    f) provide a useful amount of fodder during the winter period;
    g) have a yellow seed coat;
    h) have minimal anthocyanin expression anywhere on the plant;
9. A fodder radish according to paragraph 8 that contains genetic introgression from other species such as *Brassica*.
10. Seeds, pollen, ovules, vegetative propagules of the fodder *Raphanus* plant according to any one of paragraphs 1-9.

11. *Raphanus* seed designated PG545.
12. *Raphanus* seed having all the physiological and morphological characteristics of the *Raphanus* plant derived from the seed of the *Raphanus* PG545.
13. A method for producing a hybrid *Raphanus* seed which seed produces a plant capable of being multiple grazed, comprising crossing a first parent *Raphanus sativus* plant with a second parent *Raphanus* plant and harvesting the resultant hybrid *Raphanus*.
14. Hybrid seed produced by the method of paragraph 13.
15. A hybrid plant or its parts produced by growing hybrid seed of paragraph 14.
16. A method for the production of *Raphanus* with the ability to regrow after grazing to be suitable for multiple grazing which comprises:
    a) crossing or backcrossing *Raphanus sativus* with *Raphanus maritimus* to produce hybrid plants
    b) selecting for low crown and improved recovery from grazing in the progeny over subsequent generations
17. A method of the production of *Raphanus* cultivars with glabrous leaves which comprises:
    a) crossing or backcrossing the common phenotype with trichomes on the leaves of *Raphanus* with *Raphanus* plants containing genes for glabrous leaves to produce hybrid plants
    b) selecting for the presence of glabrous leaves in the progeny of subsequent generations
18. A method of the production of *Raphanus* with an extremely late flowering behaviour which comprises:
    a) crossing or backcrossing the common early flowering *Raphanus* with extremely late flowering *Raphanus* plants to produce hybrid plants
    b) selecting for late flowering in the progeny of subsequent generations
19. A plants or its parts producing tetraploid seed or pollen for the production of tetraploid seed of the fodder *Raphanus* which can be multiply grazed by livestock.
20. An ovule of the tetraploid plants and vegetative propagules of the tetraploid plants of paragraph 19.
21. A tetraploid *Raphanus* plant having all the physiological and morphological characteristics of a *Raphanus* plant derived from the seed of the *Raphanus* which can be multiply grazed by livestock.
22. A method for producing a tetraploid hybrid *Raphanus* seed comprising crossing a tetraploid first parent *Raphanus* plant with a second parent tetraploid *Raphanus* plant and harvesting the resultant hybrid *Raphanus* seeds, wherein said first or second parent *Raphanus* plant a tetraploid *Raphanus* plant which can be multiply grazed by livestock.
23. A tetraploid hybrid seed produced by any method of paragraph 22.
24. A tetraploid hybrid plant or its parts produced by growing hybrid *Raphanus sativus* seed produced by the method of paragraph 22.
25. Vegetative propagules of tetraploid plants according to paragraph 24.
26. A *Raphanus* plant grown from the seed PG545 or any seed having these characteristics such as, for example PG534 and PG560.

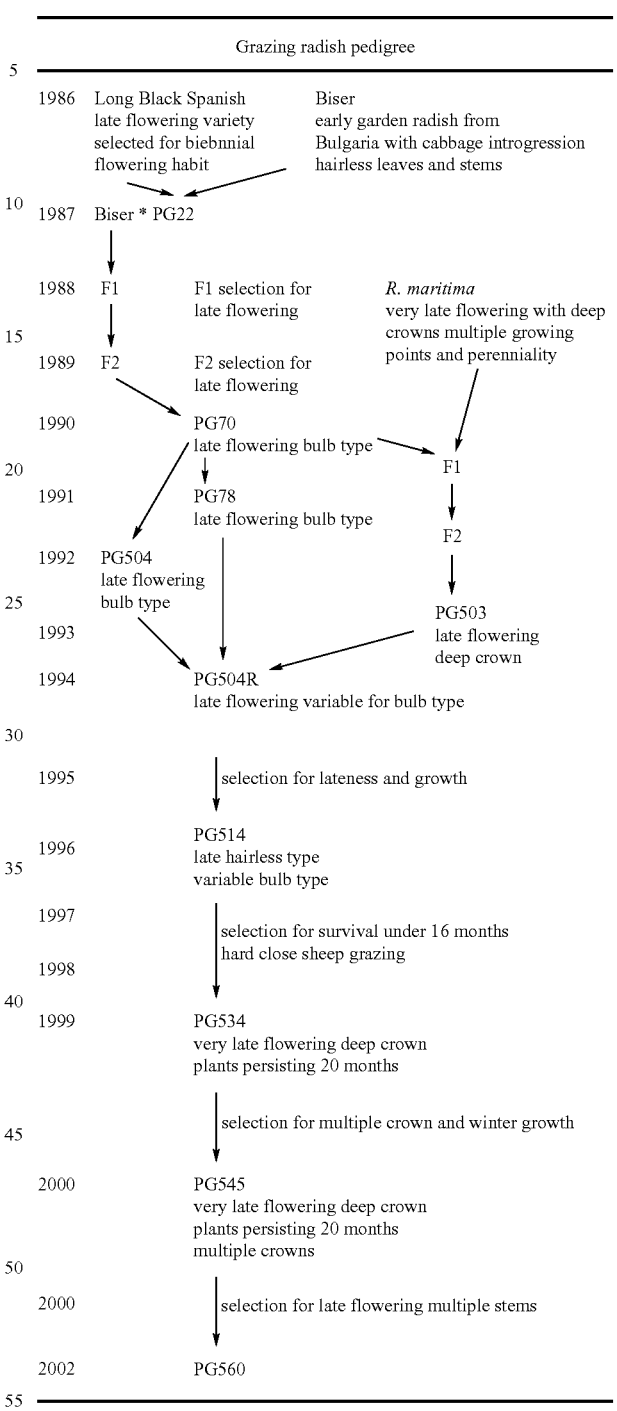

TABLE 1

Grazing radish pedigree

REFERENCES

Bonnet A 1979 Inheritance of some characters in radish (*Raphanus sativus*). *Cruciferae Newsletter* 4: 31

George R A T, Evans D R 1981 A classification of winter radish cultivars *Euphytica* 30: 483-492

Johnston T D 1963 The fodder radish. Welsh Plant breeding Station Annual Report 1963: 135-139

Johnston T D 1977 Breeding aspects of *Raphanus* and *Brassica*. *Cruciferae Newsletter* 2: 13

McNaughton I H 1976 The possibility of leafy, biennial radishes from hybridisation of *Raphanus sativus* (fodder radish) and *R. maritimus* (sea radish). *Cruciferae Newsletter* 1: 21-22

Rethman N F G, Heyns G 1987 Grazing of *Raphanus sativus* L (Japanese radish) Journal of the Grassland Society of South Africa 4:154

Verschoor A, Rethman N F G 1992 Forage potential of Japanese radish (*Raphanus sativus*) as influenced by planting date and cultivar choice. Journal of the Grassland Society of South Africa 9:176-177

What is claimed is:

1. A fodder *Raphanus* plant which can be grazed more than once by livestock, wherein the plant is selected from the group consisting of lines PG534, PG545 and PG560, a representative sample of said lines deposited under the terms of the Budapest Treaty with the Agricultural Research Service Culture Collection (NRRL).

2. Seeds, pollen, ovules, and vegetative propagules of the fodder *Raphanus* plant according to claim 1.

3. A method for producing fodder *Raphanus*, which method comprises:
   (a) crossing or backcrossing the plant of claim 1 with another fodder *Ranhanus* plant to produce hybrid plants; and
   (b) selecting for the desired phenotype in the progeny of the hybrid fodder *Raphanus* plant of subsequent generations;
   wherein the desired phenotype is a plant which:
   i) is very late flowering or biennial;
   ii) allows grazing over a longer period than more rapidly flowering or annual crops;
   iii) has a low crown;
   iv) has multiple grazing points; and
   v) has minimal leaf and stem trichomes.

* * * * *